US009579371B2

(12) United States Patent
Cardona Iglesias et al.

(10) Patent No.: US 9,579,371 B2
(45) Date of Patent: Feb. 28, 2017

(54) INACTIVATED MYCOBACTERIA FOR ORAL USE IN THE PREVENTION OF TUBERCULOSIS

(71) Applicants: FUNDACIÓ INSTITUT PER A LA INVESTIGACIÓ EN CIÈNCIES DE LA SALUT "GERMANS TRIAS I PUJOL" (IGTP), Barcelona (ES); CIBER DE ENFERMEDADES RESPIRATORIAS (CIBERES), Palma de Mallorca (Illes Balears) (ES)

(72) Inventors: Pere-Joan Cardona Iglesias, Barcelona (ES); Cristina Vilaplana Massaguer, Barcelona (ES); Elena Marzo Escartin, Santa Coloma de Farners (ES)

(73) Assignees: FUNDACIO INSTITUT PER A LA INVESTIGACIO EN CIENCIES DE LA SALUT "GERMANS TRIAS I PUJOL" (IGTP), Barcelona (ES); CIBER DE ENFERMEDADES RESPIRATORIAS (CIBERES), Palma de Mallorca (Illes Balears) (ES)

( * ) Notice: Subject to any disclaimer, the term of this patent is extended or adjusted under 35 U.S.C. 154(b) by 49 days.

(21) Appl. No.: 14/407,179

(22) PCT Filed: Jun. 13, 2013

(86) PCT No.: PCT/ES2013/000145

§ 371 (c)(1),
(2) Date: Dec. 11, 2014

(87) PCT Pub. No.: WO2013/186409

PCT Pub. Date: Dec. 19, 2013

(65) Prior Publication Data

US 2015/0174229 A1 Jun. 25, 2015

(30) Foreign Application Priority Data

Jun. 15, 2012 (ES) .................................. 201200640

(51) Int. Cl.
*A61K 39/04* (2006.01)
*A61K 39/00* (2006.01)

(52) U.S. Cl.
CPC ......... *A61K 39/04* (2013.01); *A61K 2039/521* (2013.01); *A61K 2039/542* (2013.01); *A61K 2039/545* (2013.01); *A61K 2039/577* (2013.01)

(58) Field of Classification Search
None
See application file for complete search history.

(56) References Cited

U.S. PATENT DOCUMENTS

| | | | | |
|---|---|---|---|---|
| 2005/0175630 A1* | 8/2005 | Raz | A61K 39/0208 | 424/203.1 |
| 2010/0112007 A1* | 5/2010 | Lighter | A61K 39/04 | 424/248.1 |

OTHER PUBLICATIONS

Cross et al., "Murine cytokine responses following multiple oral immunizations using lipid-formulated mycobacterial antigens," Immunology and Cell Biology (2008) 86, 214-217.

Yeboah et al., "Evaluation of albumin microspheres as oral delivery system for *Mycobacterium tuberculosis* vaccines," Journal of Microencapsulation, Mar. 2009; 26(2): 166-179.

Dlugovitzky et al., "Immunotherapy with oral, heat-killed, *Mycobacterium vaccae* in patients with moderate to advanced pulmonary tuberculosis," Immunotherapy (2010) 2(2), 159-169.

Ballesteros et al., "First data on Eurasian wild boar response to oral immunization with BCG and challenge with a *Mycobacterium bovis* field strain," Vaccine, Sep. 9, 2009, vol. 27(48), 6662-6668.

Grosset, "Studies in short-course chemotherapy for tuberculosis. Basis for short-course chemotherapy," Chest 1981: 80; 719-720.

Grosset, "*Mycobacterium tuberculosis* in the Extracellular Compartment: an Underestimated Adversary," Antimicrobial Agents and Chemotherapy, Mar. 2003, 833-836.

Opie et al., "Protective inoculation against Human tuberculosis with heat-killed tubercle bacilli," Am. J. Hyg., 1939, 29, 155-164.

Agger et al., "Specific Acquired Resistance in Mice Immunized with Killed Mycobacteria," Scand. J. Immunol. 2002, 56, 443-447.

Gupta et al., "Immunogenicity and Protective Efficacy of "*Mycobacterium w*" against *Mycobacterium tuberculosis* in Mice Immunized with Live versus Heat-Killed *M. w* by the Aerosol or Parenteral Route," Infection and Immunity, Jan. 2009, 223-231.

Hernandez-Pando et al., "Orally Administered *Mycobacterium vaccae* Modulates Expression of Immunoregulatory Molecules in BALB/c Mice with Pulmonary Tuberculosis," Clin. Vaccine Immunol. 208, 15(11): 1730-1736.

Kursar et al., "Cutting Edge: Regulatory T Cells Prevent Efficient Clearance of *Mycobacterium tuberculosis*," J. Immunology, 2007, 178, 2661-2665.

George et al., "Suppression of early atherosclerosis in LDL-receptor deficient mice by oral tolerance with β2-glycoprotein I," Cardiovascular Research 62 (2004) 603-609.

Harats et al., "Oral Tolerance With Heat Shock Protein 65 Attenuates *Mycobacterium tuberculosis*-Induced and High-Fat-Diet-Driven Atherosclerotic Lesions," Journal of the American College of Cardiology, vol. 40, No. 7, Oct. 2, 2002, 1333-1338.

Stanford et al., "Mycobacteria and their world," Intl. Journal of Mycobacteriology I (2002) 3-12.

Harper et al., "Mouse Model of Necrotic Tuberculosis Granulomas Develops Hypoxic Lesions," J. Infect. Dis. Feb. 15, 2012: 205, 595-602.

Sissons et al, "Multigenic control of tuberculosis resistance: analysis of a QTL on mouse chromosome 7 and its synergism with sst1," Genes and Immunity (2009) 10, 37-46.

Faria et al., "Oral tolerance," Immunological Reviews 205, vol. 206: 232-259.

Hori et al., "Control of Regulatory T Cell Development by the Transcription Factor Foxp3," Science vol. 299, Feb. 14, 2003, 1057-1061.

International Search Report for PCT/ES2013/000145 mailed Sep. 16, 2013.

* cited by examiner

*Primary Examiner* — Oluwatosin Ogunbiyi
(74) *Attorney, Agent, or Firm* — RatnerPrestia

(57) ABSTRACT

An inactivated mycobacteria for oral use in the prevention of tuberculosis, which are administered using a multi-dose regimen and with a reduced time interval between doses, such as to induce a tolerance-building to infection by the tubercle *bacillus*. The inactivated bacteria can be used with the aforementioned regimen to control the progression of the infection from a latent state to active tuberculosis.

14 Claims, 8 Drawing Sheets

1

2

INACTIVATED MYCOBACTERIA FOR ORAL USE IN THE PREVENTION OF TUBERCULOSIS

CROSS REFERENCE TO RELATED APPLICATIONS

This application is the U.S. National Phase Application of PCT/ES2013/000145, filed Jun. 13, 2013, which claims benefit of Spanish Patent Application No. P 201200640, filed Jun. 15, 2012, the contents of such applications being incorporated by reference herein.

FIELD OF THE ART

The present invention is comprised in the field of medicinal products administered orally to prevent tuberculosis, particularly to controlling conversion of the latent infection into the active infection of said disease.

PRIOR ART

Tuberculosis is a chronic infectious disease caused by bacteria belonging to the group *Mycobacterium tuberculosis*-complex (MTB-C), currently including the bacilli *M. tuberculosis, M. bovis, M. microti* and *M. africanum, M. tuberculosis* being the most important and most common agent in relation to human tuberculosis. Said disease primarily affects the lungs, although in some cases it can also spread to other organs. If not suitably treated, tuberculosis can be fatal.

According to the 2011 World Health Organization report, every year 9 million new cases of people presenting the disease are recorded worldwide, and about 1.7 million deaths are reported. It is also considered that there are over 2,500 million people infected around the world and about 100 million new infections are generated every year.

Tuberculosis is transmitted by air, such that patients with a tuberculous cavity in their lungs are the main source of transmission of this disease, as described, for example, in J. Grosset, *Studies in short-course chemotherapy for tuberculosis. Basis for short-course chemotherapy*, Chest, 1981, 80, 719-720, and in J. Grosset, *Mycobacterium tuberculosis in the Extracellular Compartment: an Underestimated Adversary*, Antimicrob. Agents Chemother., 2003, 47, 833-836.

As described in said papers, patients expel, by means of coughing or sneezing, a large amount of microdrops that can transport bacilli, which can enter the alveolar space of the person who inhales them.

After inhalation, the *bacillus* is phagocytized by alveolar macrophages, and inside this cell the *bacillus* can grow to the extent of causing cell destruction. The *bacillus* is phagocytized again in the extracellular space by new macrophages and this process repeats until, once they are drained and infection is generated in the hilar lymph nodes, an immune response based on cellular immunity is generated.

About 6 weeks after infection, bacillary growth ceases, the host gives a positive skin tuberculin test, characterized by a delayed type hypersensitivity (DTH) response, and so-called caseous necrosis is generated at the point of infection.

One of the main characteristics of tuberculous infection is the fact that *M. tuberculosis* is capable of remaining in the host's tissue for years, without developing the disease, in the form of "latent" tuberculous infection, but maintaining its possibilities of generating active tuberculosis.

This latent state of the infection is related to the onset of the so-called caseous necrosis, which is generated in the initial alveolar lesion and in the surrounding lung tissue, resulting in destruction of the macrophages containing the bacilli that are multiplying, causing a solid necrotic lesion.

The origin of this necrotic reaction is not precisely known, but it is related to the DTH type reaction. Essentially, the immune response that allows controlling the bacillary population is a cell type immune response primarily led by Th1 CD4, i.e., it is capable of generating a DTH type response and to also identify infected macrophages and activate them to destroy the bacilli therein.

In about 10% of infected individuals, said solid necrosis softens, which is one of the most important episodes in the tuberculous infection, since it is then when the infection progresses to active tuberculosis, i.e., a tuberculous disease.

In most cases, the softening is associated with the draining of the softened tissue towards the bronchial tree, forming a tuberculous cavity, and explosive extracellular growth of the *bacillus*, with the entrance of oxygen through the bronchial opening. With a cough, this softened caseum full of bacilli is spread to other parts of the bronchi, lungs and outside the body.

Pharmacological treatment of tuberculosis is characterized as being a prolonged therapy, which complicates treatment adherence while at the same time favors the onset of drug-resistant bacteria.

It is considered that the best strategy for containing tuberculosis is based on a preventive approach.

The current vaccine, which is administered parenterally, used in preventive treatment against tuberculosis is based on bacteria of the strain called BCG (*bacillus* Calmette-Guerin), an attenuated variant of *M. bovis*. However, it has been seen that its efficacy drops over time and that it is ineffective in prevention of the disease in adults. In fact, it is considered that it protects only the niches of the development of a fatal tuberculous disease (miliary tuberculosis or tuberculous meningitis).

Other prophylactic treatments of tuberculosis primarily based on other strains of live attenuated mycobacteria or on bacterial subunits have been developed.

Furthermore, prophylactic treatments of tuberculosis based on inactivated mycobacteria have also been studied in the state of the art for the purpose of obtaining an immune response similar to the immune response obtained with vaccines based on attenuated mycobacteria, i.e., interferon-γ producing Th1.

Therefore, for example, the paper by Opie et al., *Protective inoculation against human tuberculosis with heat-killed tubercle bacilli*, Am. J. Hyg., 1939, 29, 155-164, describes a clinical study in which five doses of bacilli *M. tuberculosis* inactivated by heating were administered intracutaneously for the purpose of generating protection against the disease.

Furthermore, the paper by Agger et al., *Specific acquired resistance in mice immunized with killed mycobacteria*, Scand. J. Immunol., 2002, 56, 443-447, describes an experimental study with mice vaccinated with three subcutaneously administered doses of 1000 μg of bacilli *M. tuberculosis* inactivated by heating, with a 2-week interval between each dose, showing an induction of specific T-cell based immunity.

Other inactivated mycobacteria have also been tested for inducing protection against tuberculosis, normally parenterally.

For example, Gupta et al., *Immunogenicity and protective efficacy of "Mycobacterium w" against Mycobacterium tuberculosis in mice Immunized with live versus heat-killed*

*M. w by the aerosol or parenteral route*, Infect. Immun., 2009, 77 (1), 223-231, describe that live M. w mycobacteria or M. w mycobacteria inactivated by heating were administered. M. w mycobacteria inactivated by heating were subcutaneously administered as a single-dose, and an immune response based on the induction of interferon-producing Th1 cells was observed.

It is particularly desirable to provide an effective prophylactic treatment administered orally because this administration route considerably facilitates administration of the drug and treatment adherence.

In this sense, there are documents in the state of the art that refer to oral administration of bacteria inactivated by the heat of mycobacteria, *Mycobacterium vaccae*, to achieve a therapeutic effect of active tuberculosis, according to a regimen combined with the usual chemotherapy drugs.

At the experimental level, Hernández-Pando et al., *Orally administered Mycobacterium vaccae modulates expression of immunoregulatory molecules in BALB/c mice with pulmonary tuberculosis*, Clin. Vaccine Immunol., 2008, 15(11), 1730-1736, describe an assay conducted on mice to which 5 doses of 0.1 μg of *M. vaccae* inactivated by heating were administered orally, with a 28-day interval between each administration, inducing infection with *M. tuberculosis* intratracheally 23 hours after the first dose. It was confirmed in said study that a cellular immune response was generated, increasing Th1 cell secretion, while humoral immunity dropped, as demonstrated by a reduction of Th2 type cells and TGF-beta growth factor.

Generally, the state of the art suggests that Th1 induction, with subsequent interferon-γ production, is desirable, whereas a Th2 response, with subsequent IL-4 production, or Th3 response, which entails regulatory T cell (Treg) production, can have an active tuberculosis-inducing effect.

This is described, for example, in Kursar et al., *Cutting Edge: Regulatory T Cells Prevent Efficient Clearance of Mycobacterium tuberculosis*, J. Immunol., 2007, 178, 2661-2665, in which the production of regulatory T cells (Treg) is attributed to the inability of CD4 T cells to sterilize caseous lesions and prevent latent infection in the mouse model of experimental tuberculosis. Said paper suggests that deregulation allowing the imbalance between the Th1 response and Treg response in favor of the Treg response can be the cause of active tuberculosis induction.

In view of what has been described in the state of the art, there continues to be a need to provide effective treatment for tuberculosis that can be administered orally to prevent the development of active tuberculosis, and the subsequent onset of the pathological state of the disease both in non-infected individuals (prophylactic effect) and in individuals infected by *M. tuberculosis* in which the infection is in a latent state (therapeutic effect).

OBJECT OF THE INVENTION

The object of the present invention is the use of inactivated mycobacteria for preparing a medicinal product for oral administration to prevent tuberculosis.

DETAILED DESCRIPTION OF THE INVENTION

Figure 1:
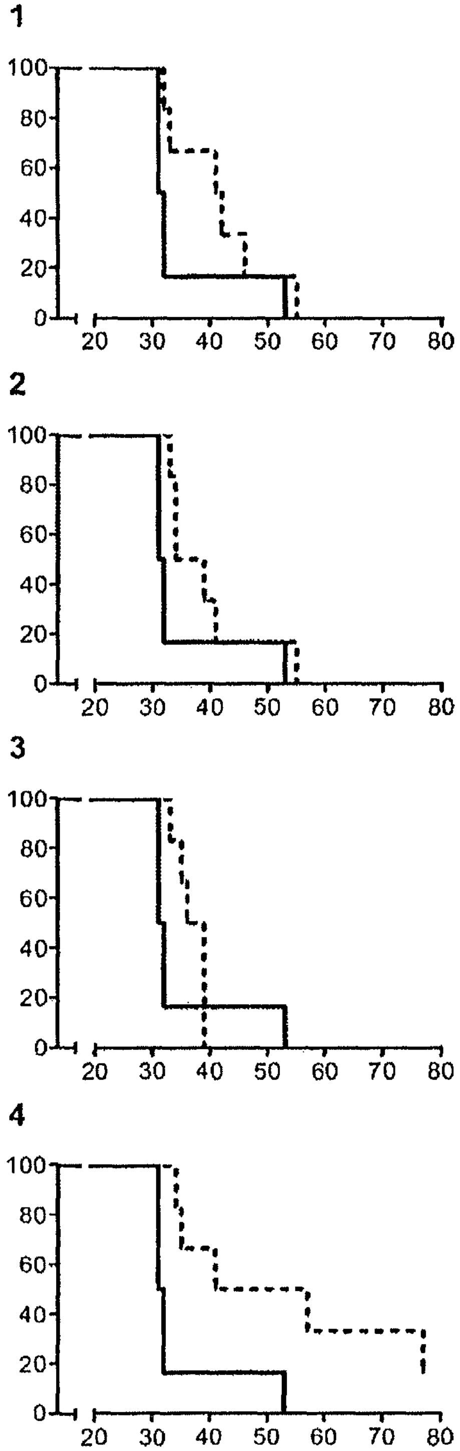
FIG. 1 shows the time of survival expressed in days represented on the x-axis and the percentage of surviving animals represented on the y-axis. The Control Group is represented with a solid line, and the animals in Group 1 are represented with a discontinuous line. Animals in Group 1 were subjected to oral treatment with inactivated mycobacteria of *Mycobacterium tuberculosis* before infection by means of the administration of 5 doses of said bacilli, one every 48 hours starting on day 10 before infection. Graphs 1, 2, 3 and 4 correspond to animals in Groups 1a, 1b, 1c and 1d, respectively, to which different amounts of product were administered according to 1:1, 1:10, 1:100 and 1:1000 dilutions. (Example 1)

The object of the present invention is the use of inactivated mycobacteria for preparing a medicinal product to prevent tuberculosis, wherein:

- the inactivated mycobacteria are periodically administered orally,
- the interval between doses is not more than 5 days, and
- the number of doses administered is at least 5.

Alternatively, the object of the present invention can be formulated as inactivated mycobacteria for use to prevent tuberculosis, wherein:

- the mycobacteria are periodically administered orally,
- the interval between doses is not more than 5 days, and
- the number of doses administered is at least 5.

The authors of the present invention have developed a new preventive treatment against tuberculosis which is based on the administration of inactivated mycobacteria using a multi-dose regimen administered with a reduced time interval between administrations.

The authors have observed that said preventive treatment administered before infection by *M. tuberculosis* (prophylactic effect) or after infection (therapeutic effect) is capable of preventing the development of active tuberculosis by means of controlling progression of the infection from a latent state to active tuberculosis.

According to said treatment, periodic oral administration of dead bacilli, preferably at low doses, and with a reduced time interval between doses, induces tolerance-building or a tolerance-building response which surprisingly has a positive effect on controlling infection by *M. tuberculosis*, i.e., on controlling conversion of the latent infection into the active infection.

The authors have in fact observed that such treatment administered both before and after infection by *M. tuberculosis* triggers a tolerance-building response characterized by an increase in the percentage of regulatory T cells (Treg).

The use of the invention focuses on non-infected individuals and individuals infected by *M. tuberculosis* in which the infection is in a latent state. In the case of non-infected individuals, preventive treatment is considered to have a prophylactic effect, whereas in the case of individuals infected by *M. tuberculosis* it is considered to have a therapeutic effect.

A particular aspect of this second case, i.e., preventive treatment with a therapeutic effect (referring to a subjects infected by *M. tuberculosis* in which the infection is in a latent state), consists of those individuals who had previously developed active tuberculosis and in which said disease subsequently remitted, for example by means of treatment with conventional anti-tuberculous therapy, the tuberculosis therefore having reverted back to a latent infection state. This particular case of preventive treatment is considered to have a therapeutic anti-relapse effect.

In the case of preventive treatment with anti-relapse effect, therefore, individuals were normally previously subjected to pharmacological treatment with anti-tuberculous agents. These anti-tuberculous agents are well known by the person skilled in the art, the primary anti-tuberculous agents being, for example, isoniazid, ethambutol, pyrazinamide, rifampicin, streptomycin; and those second line anti-tuberculous agents applied in the case of the onset of resistances, for example, thioamides (prothionamide, ethionamide, among others), aminoglycosides (amikacin, kanamycin, among others), cycloserine, rifabutin, rifapentine, fluorquinolones (moxifloxacin, levofloxacin, ofloxacin), PAS, clarithromycin, clofazimide, linezolid or thioridazine among others, or mixtures thereof.

"Preventive treatment" is generally understood as that treatment which allows protecting an individual from a disease.

In this sense, in the context of the invention, preventive treatment is that treatment capable of preventing the development of active tuberculosis by means of controlling conversion of the latent infection into the active infection.

"Tolerance-building" is generally understood as the intentional induction of tolerance by means of biological or chemical agents, wherein the term "tolerance" means a state of low response specific to the biological or chemical agent.

Therefore, in the context of the invention the expression "induction of a tolerance-building response" is understood as a method whereby a state of a lack of response to a specific antigen is induced in the host immune system, resulting in attenuation of the disorder.

Tolerance-building regimens have been described in the state of the art in the context of other diseases such as, for example, atherosclerosis. George et al., *Suppression of early atherosclerosis in LDL-receptor deficient mice by oral tolerance with h2-glycoprotein I*, Cardiovasc. Res., 2004, 62, 603-609, describe the use of β2-glycoprotein I for inducing oral tolerance and suppressing early atherosclerosis, and Harats et al., *Oral Tolerance With Heat Shock Protein 65 Attenuates Mycobacterium Tuberculosis-Induced and High-Fat-Diet-Driven Atherosclerotic Lesions*, J. Am. Coll. Cardiol., 2002, 40, 1333-1338, describe the use of heat shock protein 65 for inducing oral tolerance to atherosclerotic lesions.

Inactivated Mycobacteria

The genus of the mycobacteria belongs to the family of Mycobacteriaceae and is formed by aerobic bacilli.

All the bacilli belonging to the genus of the mycobacteria are part of the object of the present invention, for example the species *M. abscessus, M. africanum, M. asiaticum, M. aurum, M. avium, M. avium paratuberculosis, M. avium silvaticum* and *M. avium hominissuis, M. bovis, M. bovis* BCG, *M. chelonae, M. fortuitum, M. gastri, M. goodi, M. gordonae, M. immunogenum, M. haemophilum, M. habana, M. kansasii, M. lentiflavum, M. leprae, M. lepromatosis, M. lufu, M. mageritense, M. malmoense, M. marinum, M. massiliense, M. microti, M. monacense, M. mucogenicum, M. neoaurum, M. peregrinum, M. phlei, M. scrofulaceum, M. smegmatis, M. terrae, M. triviale, M. tuberculosis, M. microti, M. ulcerans, M. vaccae* and *M. xenopi*, among others.

Mycobacteria have many antigens in common with *M. tuberculosis* and are therefore suitable for the use of the present invention. The paper by Stanford et al., *Mycobacteria and their world*, Int. J. Mycobacteriol., 2012, 3-12, describes a classification of the different groups of antigens in mycobacteria and how they are distributed and shared between different species of the family Mycobacteriaceae.

The inactivated mycobacteria that are part of the present invention are preferably: mycobacteria of the group called *Mycobacterium tuberculosis* complex (MTB-C), *Mycobacterium fortuitum* and *Mycobacterium kansasii*. In other words, the inactivated mycobacteria are preferably selected from the group consisting of *M. tuberculosis, M. bovis, M. africanum*, and *M. microti, M. bovis* BCG, *M. fortuitum* and *M. kansasii*. The inactivated mycobacteria are more preferably selected from the group consisting of *M. tuberculosis, M. bovis, M. bovis* BCG, *M. fortuitum* and *M. kansasii*.

Inactivated mycobacteria, also referred to as dead mycobacteria, are understood to be those mycobacteria that have been subjected to physical or chemical treatment transforming the live mycobacteria into a form that is unable to replicate.

Within the scope of the present invention, suitable methods for inactivating the mycobacteria are, for example, treatment with formaldehyde, irradiation treatment or heat treatment.

The inactivated mycobacteria object of the present invention are preferably inactivated by means of a heating process.

A suitable method for inactivating mycobacteria by heating comprises, for example, culturing a strain of the mycobacteria in a suitable culture medium, as they are well known by the person skilled in the art, such as the Middlebrook 7H10 or 7H11 agar, Sauton medium or Proskauer-Beck medium, among others. The culture is preferably maintained until achieving a concentration comprised between about $1\times10^5$ and $1\times10^9$ colony forming units (CFUs) per ml.

The culture is then inactivated by heating. The culture is preferably heated at a temperature comprised between 70° C. and 90° C. The heating period is preferably comprised between 30 minutes and 3 hours. Furthermore by means of using an autoclave, the culture preferably being heated at a temperature of 121° C. for 20 minutes.

Prevention of Tuberculosis

The expression "prevention of tuberculosis" refers to preventing the manifestation of active tuberculosis by means of controlling progression of the infection from a latent state to active tuberculosis.

Said prevention can be performed in non-infected individuals and also in individuals infected by *M. tuberculosis* in which the infection is in a latent state, either because the disease has not yet developed or because the active disease had already developed and later remitted, for example due to treatment with anti-tuberculous drugs.

The authors of the present invention have developed a preventive treatment against tuberculosis which prevents progression of the latent infection, such that the progression of the solid caseous lesions into liquefied lesions is prevented, and manifestation of active tuberculosis is therefore prevented.

The authors of the present invention have used an experimental model based on the use of C3HeB/FeJ mice, in which a lung pathology after infection by *M. tuberculosis*, equivalent to that which is developed in humans, can be simulated.

Formation of caseous necrosis which can liquefy in response to infection with *M. tuberculosis*, unlike what occurs in other animal models that do not develop said necrosis, is observed in said animals, as described in the paper by Harper et al., *Mouse model of necrotic tuberculosis granulomas develops hypoxic lesions*, J. Infect. Dis., 2012, 205, 595-601.

In the event of being endovenously infected with a high dose, growth of necrosis and of the lesions in said animals is such that it can cause 100% mortality about four weeks after infection, as described in the paper by Sissons et al., *Multigenic control of tuberculosis resistance: analysis of a QTL on mouse chromosome 7 and its synergism with sst1*, Genes Immun., 2009, 10, 37-46.

Without wanting to be bound by any theory, the authors of the present invention consider that the preventive effect of the treatment object of the present invention is because the oral administration of frequent periodic doses of dead bacilli, preferably at low doses, is a regimen that can induce tolerance in subjects, generating a response in which regulatory T cells (Tregs) are preferably induced. Said cells are related to the transforming growth-factor beta (TGF-beta), i.e., a tolerance-building or Th3 immune response is primarily generated, unlike conventional vaccination systems, where basically a Th1 immune response is triggered.

The authors of this invention have surprisingly found that induction of tolerance is effective for stopping progression of the infection by *M. tuberculosis*, i.e., conversion of the latent infection into the active infection.

The inactivated mycobacteria must be administered repeatedly and with reduced time intervals between each administration, i.e., not more than 5 days, to trigger this tolerance-building response; preferably, the interval between doses is not more than 3 days; and more preferably, the interval between doses is not more than 2 days.

Tolerance-building treatment also requires the repeated administration of the inactivated mycobacteria, the number of doses administered being at least 5; preferably, the number of doses administered is at least 7; more preferably, the number of doses administered is at least 9, and even more preferably, the number of doses administered is at least 14.

In the use of the invention, an immunologically effective amount of inactivated mycobacteria is administered.

The dose to be used is known to be dependent on the age and weight of the individual to whom the mycobacteria are administered.

Suitable doses are generally comprised in the range between $10^3$ and $10^{10}$ inactivated mycobacteria, preferably between $10^3$ and $10^8$, and more preferably between $10^4$ and $10^8$.

To demonstrate the preventive therapeutic effect on caseous lesion liquefaction of the tolerance-building dosing regimen that is part of the present of invention, the C3HeB/FeJ mice used in the model described above were subjected to a protocol in which between 5 and 14 doses of inactivated mycobacteria were administered orally with an interval between doses comprised between 1 and 3 days.

The murine model used simulates preventive tuberculosis therapy either when treatment is administered before infection, as described in Examples 1 and 3-6, or when treatment is started after infection by *M. tuberculosis*, as described in Examples 1, 2, and 4-6, but said treatment is administered in an early stage (up to 15 days after infection when the animals have already developed lesions, but the lesions have still not progressed to liquefaction and subsequent manifestation of the disease); or alternatively, as described in Example 7, treatment is administered after infection when the animals have developed lesions and the lesions have liquefied, but said lesions have returned to the form of small lesions characteristic of latent infection.

Based on the results obtained in the examples, it is concluded that oral administration of tolerance-building regimens of inactivated mycobacteria both before and after infection by *M. tuberculosis* increases animal survival because induction of the disease, i.e., conversion of the latent infection into the active infection, is delayed.

It is therefore considered that the use of inactivated mycobacteria according to the present invention is suitable to prevent tuberculosis.

Compositions

According to the object of the present invention, the inactivated mycobacteria are administered orally.

Said mycobacteria can be administered in the form of any pharmaceutical composition suitable for oral administration, as is well known by the persons skilled in the art. For example, tablets, capsules, solutions, suspensions, dispersions, powders, granules, or sprays are suitable for oral administration.

The mycobacteria are preferably administered in capsule or tablet form.

The pharmaceutical compositions generally comprise inactivated mycobacteria and at least one pharmaceutically acceptable excipient.

The compositions are prepared according to conventional methods well known by the person skilled in the art, such as those found in pharmaceutical technology manuals, such as the textbook, Remington The Science and Practice of Pharmacy, $20^{th}$ edition, Lippincott, Williams & Wilkins, Philadelphia, 2000 [ISBN: 0-683-306472].

Among the pharmaceutically acceptable excipients that can be included in the pharmaceutical composition are, for example, anti-caking agents such as colloidal silica, calcium phosphate tribasic, calcium silicate, magnesium silicate, magnesium trisilicate or talc; diluting agents such as lactose anhydrous, lactose monohydrate, calcium phosphate, calcium hydrogen phosphate anhydrous, calcium hydrogen phosphate dihydrate, calcium sulfate, calcium carbonate, carboxymethyl cellulose calcium, microcrystalline cellulose or cellulose powder, cellulose acetate, dextrates, dextrins, dextrose, fructose, glyceryl palmitostearate, kaolin, lactitol, magnesium carbonate, magnesium oxide, maltitol, maltodextrins, maltose, polymethacrylates, pregelatinized starch, sodium chloride, starch, sucrose; lubricating agents such as magnesium stearate, calcium stearate, glycerin palmitostearate, poloxamers, magnesium oxide, sodium benzoate, colloidal silica, sodium lauryl sulfate, sodium stearyl fumarate, stearic acid, talc or glyceryl behenate; suspending agents such as xanthan gum, guar gum, alginic acid, bentonite, carbomers, carboxymethyl cellulose sodium or calcium, hydroxyethyl cellulose, hydroxypropyl cellulose, hydroxypropyl methylcellulose, hydroxypropyl alginate, microcrystalline cellulose or cellulose powder, colloidal anhydrous silica, dextrins, gelatins, kaolin, magnesium aluminum silicate, maltitol, povidone, sorbitan esters or tragacanth; binding agents such as magnesium trisilicate, cellulose, starch, dextrin, dextrose, polydextrose, maltose, maltodextrin, ethyl cellulose, methyl cellulose, polymethacrylates, talc, povidone, stearic acid or sucrose; disaggregating agents such as low-substituted hydroxypropyl cellulose, calcium phosphate tribasic, carboxymethyl cellulose sodium or calcium, croscarmellose sodium, crospovidone or methyl cellulose; coating agents such as chitosan, dibutyl phthalate, dibutyl sebacate, diethyl phthalate, dimethyl phthalate, ethyl cellulose, hydroxyethyl cellulose, hydroxypropyl cellulose, hypromellose, maltodextrin, polymethacrylates, polyvinyl acetate phthalate, or triethyl citrate; dispersing agents such as poloxamers or sorbitan esters; sweetening agents such as aspartame, mannitol, sorbitol, sodium saccharine, sodium cyclamate, sucrose, dextrose, fructose, glucose, inulin, isomaltose, lactitol, maltose, maltol, mannitol, sucralose, trehalose, xylitol or thaumatin; flavoring agents and flavorings, and/or mixtures thereof.

A more thorough list of excipients, as well as their physicochemical characteristics and the names of the commercial products under which they are sold can be found in the textbook by R. C. Rowe et al., Handbook of Pharmaceutical Excipients, $4^{th}$ edition, Pharmaceutical Press, London, 2003 [ISBN: 0-85369-472-9].

The following examples seek to illustrate the invention, though they must not be interpreted as being limiting thereof.

Example 1

Oral Tolerance-Building Treatment with Inactivated Bacilli of *M. tuberculosis*, Administered Before or after Infection (Prophylactic or Therapeutic Effect)

A clinical strain of *M. tuberculosis* (TOL-3) from the Unitat de Tuberculosi Experimental of Institut Germans Trias i Pujol strain collection, cultured in Proskauer Beck liquid medium until achieving exponential growth and a concentration of $1.7\times10^7$ colony forming units (CFUs) per ml, was used to prepare the inactivated mycobacteria.

The culture was inactivated after heating at 75° C. for 2 hours and subsequently frozen at −80° C. It was subsequently diluted 50:50 in a 10% sucrose solution, packaged and lyophilized in vials in 0.5 ml volumes. These vials were subsequently reconstituted with 3 ml of bidistilled water, constituting the 1:1 dilution, which is equivalent to $4.25\times10^6$ CFUs.

In the assays, 0.3 ml of product were administered at both this 1:1 dilution and at 1:10, 1:100, and 1:1000 dilutions. These administrations correspond to several doses of $4.25\times10^5$, $4.25\times10^4$, $4.25\times10^3$ and $4.25\times10^2$ CFUs, respectively.

Effectiveness of the inactivated mycobacteria was tested in 6-8 week old C3HeB/FeJ female mice free of specific pathogens.

The mice were split into three groups with 6 animals each, and each of the groups was subjected to the following tolerance-building protocol.

1) Control Group: Untreated.
2) Group 1 (pre-infection treatment): Treated orally by gavage, with 5 product doses containing the inactivated mycobacteria, administered every 48 hours starting on day 10 before infection. A volume of 0.3 ml was administered in each dose, and a total of 4 dilutions, i.e., 1:1, 1:10, 1:100 and 1:1000 (Groups 1a, 1 b, 1c and 1 d, respectively), were tested.

3) Group 2 (post-infection treatment): Treated orally by gavage, with 5 product doses containing the inactivated mycobacteria, administered every 48 hours starting on day 11 after infection. A volume of 0.3 ml was administered in each dose, and a total of 4 dilutions, i.e., 1:1, 1:10, 1:100 and 1:1000 (Groups 2a, 2b, 2c and 2d, respectively), were tested.

The virulent strain of *Mycobacterium tuberculosis* ($H_{37}Rv$ Pasteur), cultured in Proskauer-Beck medium to mid-logarithmic phase and preserved in 1 ml aliquots at a temperature of −70° C. until use, was used for infection.

The mice were endovenously infected by introducing an inoculum of about $2\times10^4$ viable bacilli.

The animals were observed and weighed daily until conditions of the animal required it be sacrificed, according to the method described in detail in Table 1.

TABLE 1

| | Observation of the animal | Score |
|---|---|---|
| Weight | Normal (no weight loss, the animal grows as per normal) | 0 |
| | Weight loss <10% | 1 |
| | Weight loss between 10-15%. Possible change in the appearance or amount of feces | 2 |
| | Weight loss >15%. The animal does not drink water or eat food | 3 |
| Appearance | Normal | 0 |
| | Coat in poor state | 1 |
| | Coat in poor state and/or presence of ocular or nasal secretions | 2 |
| | Abnormal posture | 3 |
| Observation of signs of pain | Absence of signs (no self-mutilations or strange sounds are observed) | 0 |
| | Observation of self-mutilations or strange sounds | 3 |
| Response to stimuli | Normal (neither aggressive nor comatose) | 0 |
| | Very aggressive or comatose | 3 |

0-2: normal.
3: Increase the frequency of applying the supervision protocol to a 2 times/day.
If a score of 3 is obtained in more than one concept, all scores of 3 become scores of 4.
When one or more of the scores reaches the value of 4, the animal is sacrificed.

Figure 2:
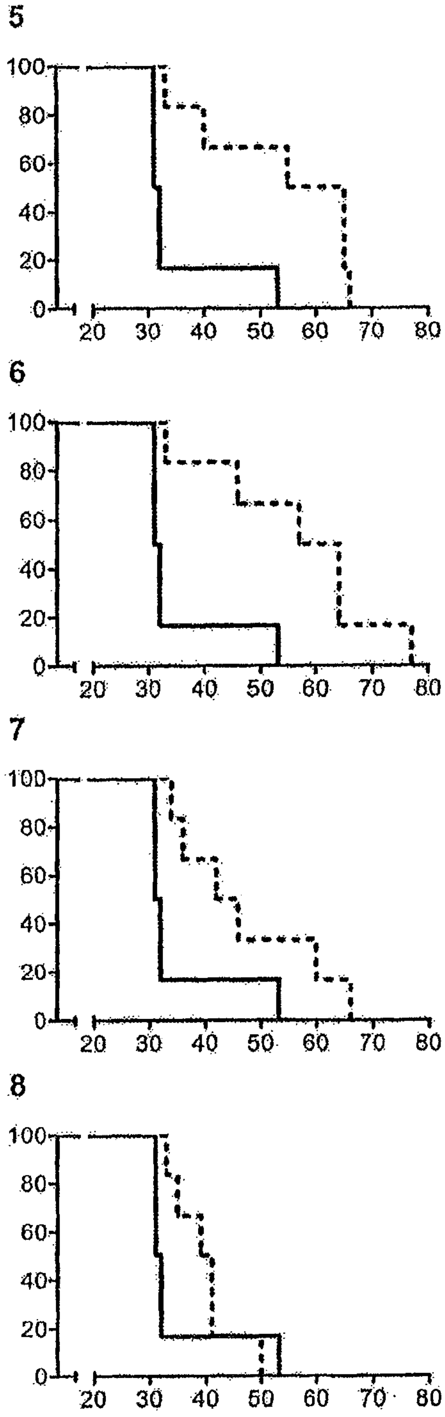
FIG. 2 shows the time of survival expressed in days represented on the x-axis and the percentage of surviving animals represented on the y-axis. In this figure, the Control Group (solid line) is compared with Group 2 (discontinuous line). Animals in Group 2 were subjected to oral treatment with inactivated mycobacteria of *Mycobacterium tuberculosis* after infection by means of the administration of 5 doses of said bacilli, one every 48 hours starting on day 11 after infection. Graphs 5, 6, 7 and 8 correspond to animals in Groups 2a, 2b, 2c and 2d, respectively, to which different amounts of product were administered according to 1:1, 1:10, 1:100 and 1:1000 dilutions. (Example 1)

The obtained results are graphically depicted in FIGS. 1 and 2, which show the progression of survival of the animals after infection for the different experimental groups. Time of survival expressed in days is represented on the x-axis, whereas the percentage of survivors is represented on the y-axis.

In FIG. 1, the Control Group (solid line) is compared with the animals in Group 1 (discontinuous line) which were treated before infection. Graphs 1, 2, 3 and 4 correspond to animals in Groups 1a, 1 b, 1c and 1 d, respectively, to which different amounts of product were administered according to 1:1, 1:10, 1:100 and 1:1000 dilutions.

In FIG. 2, the Control Group (solid line) is compared with the animals in Group 2 (discontinuous line) which were treated after infection. Graphs 5, 6, 7 and 8 correspond to animals in Groups 2a, 2b, 2c and 2d, respectively, to which different amounts of product were administered according to 1:1, 1:10, 1:100 and 1:1000 dilutions.

To evaluate the effect of treatment on survival of the animals, survival curves were compared by means of two methods: the Mantel-Cox test (or the Log-rank test, LR t) and the Gehan-Breslow-Wilcoxon test (GBW t). In the first method, it is assumed that the risk (deaths/unit of time) is constant throughout the entire experiment, whereas the second method takes the deaths in the first few days (earlier deaths) more into account. If the risk is constant, the Mantel-Cox test has higher statistical power, but if that is not the case and there is a group that is at a higher risk than the other, the Gehan-Breslow-Wilcoxon method is more suitable.

Statistically significant differences are observed in all cases ($p<0.05$, GBW t) with respect to control groups. There is also statistical significance for LR t ($p<0.05$) in the treatments corresponding to graphs 4, 5, 6 and 7.

The results reflect a protective response when the pre-infection regimen was used with the lowest dilution (1:1000, FIG. 1, graph 4), whereas protection with the post-infection regimen was observed with dilutions 1:1, 1:10 and 1:100 (FIG. 2, graphs 5, 6 and 7, respectively), being particularly important in the 1:10 dilution regimen.

Autopsies on the Control Group reflected a very rapid progression between days 26 and 30, during which period the lesions greatly increased in size and ended up converging, generating large lesions with necrosis having an inner creamy consistency.

It can therefore be concluded that oral administration of tolerance-building regimens, both before (prophylactic effect) and after (therapeutic effect) infection by *M. tuberculosis*, increases survival of the animals by delaying conversion of the latent infection into the active infection. It is therefore considered that the use of inactivated mycobacteria according to the invention is suitable as preventive treatment against tuberculosis.

Example 2

Oral Tolerance-Building Treatment with Inactivated Bacilli of *M. bovis* BCG Administered after Infection (Therapeutic Effect)

The therapeutic agent used in this example was prepared from a commercial strain of *M. bovis* BCG (SSI) cultured in Proskauer Beck liquid medium until achieving exponential growth and a concentration of $1.03\times10^8$ colony forming units (CFUs) per ml. The culture was inactivated following the same method described in Example 1.

Effectiveness of the inactivated mycobacteria was tested in 6-8 week old C3HeB/FeJ female mice free of specific pathogens. A volume of 0.3 ml corresponding to a 1:10 dilution, which corresponds to $2.575\times10^5$ CFUs, was administered in each dose.

The mice were split into two groups with 12 animals each, and each of the groups was subjected to the following tolerance-building protocol:

1) Control Group: Untreated.
2) Group 1 (post-infection treatment): Treated orally by gavage, with 5 product doses containing the inactivated mycobacteria, administered every 48 hours starting on day 12 after infection, and subsequently 3 times a week (Monday, Wednesday and Friday) until the end of the experiment, according to the time of survival of each mouse The virulent strain of *Mycobacterium tuberculosis* ($H_{37}Rv$ Pasteur), cultured in Proskauer-Beck medium to mid-logarithmic phase and preserved in 1 ml aliquots at a temperature of −70° C. until use, was used for infection.

The mice were endovenously infected by introducing an inoculum of about $2\times10^4$ viable bacilli.

The animals were observed and weighed daily until conditions of the animal required it be sacrificed, according to the same method described in Table 1 of Example 1.

Figure 3:
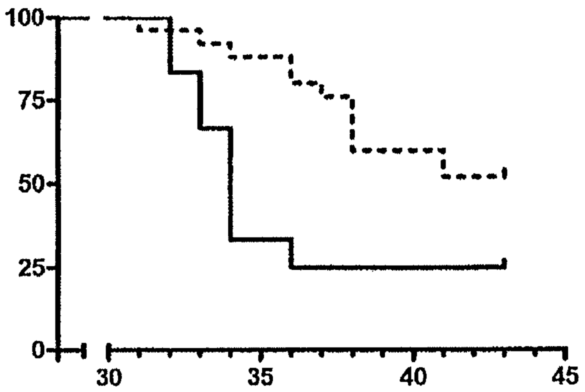
FIG. 3 shows the time of survival expressed in days represented on the x-axis and the percentage of surviving animals represented on the y-axis. In this figure, the Control Group (solid line) is compared with the animals in Group 1 (discontinuous line) which was treated orally with inactivated mycobacteria of *M. bovis* BCG after infection. (Example 2)

The obtained results are graphically depicted in FIG. 3. Time of survival (in days) is represented on the x-axis, whereas the percentage of survivors is represented on the y-axis.

It is observed that the Control Group (solid line) has a lower survival rate than treated Group 1 (discontinuous line), significant differences being observed (Log-rank test, p=0.0147; Gehan-Breslow-Wilcoxon test, p=0.0052).

The results reflect a protective response after continuous treatment of the infected animals. It can therefore be concluded that oral administration of tolerance-building regimens of inactivated *M. bovis* BCG after infection by *M. tuberculosis* increases the survival rate of the animals by delaying induction of the disease. It is therefore considered that the use of inactivated mycobacteria according to the invention is suitable as preventive treatment against tuberculosis by delaying conversion of the latent infection into the active infection.

Example 3

Oral Tolerance-Building Treatment with Inactivated Bacilli of *M. bovis* BCG Administered Pre-Infection (Prophylactic Effect)

The inactivated bacilli of *M. bovis* BCG were prepared following the same method described in Example 2.

Effectiveness of the inactivated mycobacteria was tested in 6-8 week old C3HeB/FeJ female mice free of specific pathogens.

The mice were split into two groups with 12 animals each, and they were subjected to the following treatment:

1) Control Group: Untreated.
2) Group 1 (pre-infection treatment): Treated orally by gavage, with 13 product doses containing the inactivated mycobacteria, administered 3 times a week (Monday, Wednesday and Friday) starting 29 days before infection. A volume of 0.3 ml corresponding to a 1:1000 dilution, which corresponds to $2.575\times10^3$ CFUs, was administered in each dose.

Like in the preceding examples, the virulent strain of *M. tuberculosis* ($H_{37}Rv$ Pasteur), cultured in Proskauer-Beck medium to mid-logarithmic phase and preserved in 1 ml aliquots at a temperature of −70° C. until use, was used for infection.

The mice were endovenously infected by introducing an inoculum of about $2\times10^4$ viable bacilli.

The animals were observed and weighed daily until conditions of the animal required it be sacrificed, according to the same method described in Table 1 of Example 1.

Figure 4:
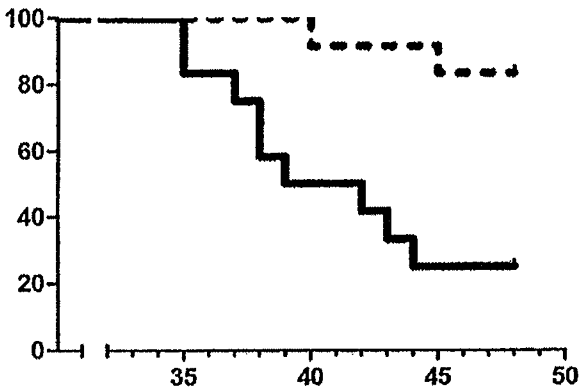
FIG. 4 shows the time of survival expressed in days represented on the x-axis and the percentage of surviving animals represented on the y-axis. In this figure, the Control Group (solid line) is compared with the animals in Group 1 (discontinuous line), which was treated orally with inactivated mycobacteria of *M. bovis* BCG before infection (Example 3)

The obtained results are graphically depicted in FIG. 4. Time of survival (in days) is represented on the x-axis, whereas the percentage of survivors is represented on the y-axis.

It is observed that the Control Group (solid line) has a lower survival rate than treated Group 1 (discontinuous line), significant differences being observed according to the Log-rank test (p=0.0020) and the Gehan-Breslow-Wilcoxon test (p=0.0019).

The results reflect a protective response after the induction of tolerance by oral administration of inactivated mycobacteria *M. bovis* BCG prior to infection by *M. tuberculosis*, observing that said treatment prevents the induction of the disease in a high percentage.

Example 4

Effectiveness of Oral Tolerance-Building Treatment with Inactivated Bacilli of *M. tuberculosis*, Administered Pre-Infection or Post-Infection (Prophylactic or Therapeutic Effect) and Monitoring the Induced Tolerance by Means of Analyzing Regulatory T Cells in the Spleen The inactivated bacilli of *M. tuberculosis* (TOL-3) were prepared following the same method described in Example 1.

Effectiveness of the inactivated mycobacteria was tested in 6-8 week old C3HeB/FeJ female mice free of specific pathogens.

The mice were split into three groups with 24 animals each, and they were subjected to the following treatment:

1) Control Group: Untreated.
2) Group 1 (pre-infection treatment): Treated orally by gavage, with 5 product doses containing the inactivated mycobacteria, administered every 48 hours, starting on day 10 before infection, and subsequently 3 times a week (Monday, Wednesday and Friday) until the end of the experiment. A volume of 0.3 ml with a 1:1000 dilution was administered with each dose.
3) Group 2 (post-infection treatment): Treated orally by gavage, with 5 product doses containing the inactivated mycobacteria, administered every 48 hours, starting on day 11 after infection, and subsequently 3 times a week (Monday, Wednesday and Friday) until the end of the experiment. A volume of 0.3 ml with a 1:10 dilution was administered in each dose.

Like in the preceding examples, the virulent strain of *M. tuberculosis* ($H_{37}Rv$ Pasteur), cultured in Proskauer-Beck medium to mid-logarithmic phase and preserved in 1 ml aliquots at a temperature of −70° C. until use, was used for infection.

The mice were endovenously infected by introducing an inoculum of about $1\times10^5$ viable bacilli.

Half the animals in each group (12) were set aside for the survival study. The animals were observed and weighed daily until conditions of the animal required it be sacrificed, according to the same method described in Table 1 of Example 1.

Figure 5:
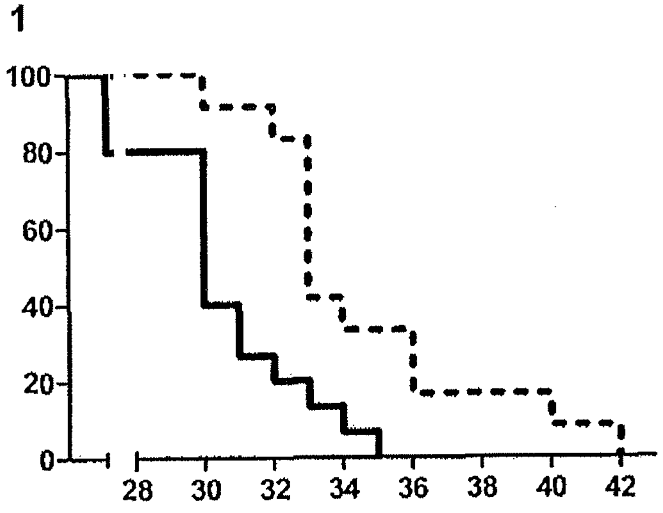
FIG. 5 shows the time of survival expressed in days represented on the x-axis and the percentage of surviving animals represented on the y-axis. In graph 1, the Control Group (solid line) is compared with Group 1 (discontinuous line) which was subjected to orally administered treatment with inactivated mycobacteria of *Mycobacterium tuberculosis* that started before infection. In graph 2, the Control Group (solid line) is compared with Group 2 (discontinuous line) which was subjected to orally administered treatment with inactivated mycobacteria that started after infection, in graph 2. (Example 4)
Figure 5:
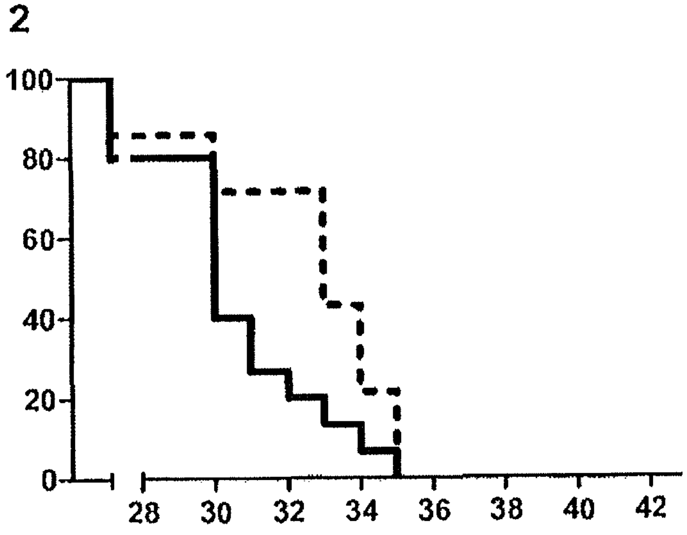

In FIG. 5, graphs 1 and 2 show the results of survival of the different experimental groups. Time of survival (in days) is represented on the x-axis, whereas the percentage of surviving animals is represented on the y-axis.

In graph 1, the Control Group (solid line) is compared with Group 1 (discontinuous line) which was subjected to treatment that started before infection. It is observed that the Control Group has a lower survival rate than the treated group, with statistically significant results according to the Log-rank test (p=0.0011) and the Gehan-Breslow-Wilcoxon test (p=0.0014).

In graph 2, the Control Group (solid line) is compared with Group 2 (discontinuous line) which was subjected to treatment that started after infection. It is observed that the Control Group has a lower survival rate than the treated group, with statistically significant results according to the Log-rank test (p=0.04541), whereas according to the Gehan-Breslow-Wilcoxon test the differences are not statistically significant.

In both cases it is concluded that the animals treated with a tolerance-building regimen with inactivated mycobacteria survive for a longer time after infection with *M. tuberculosis* than the untreated animals do.

As regards the remaining animals in each group (12), half the animals were sacrificed at week 3 (6 animals per group) and the other half at week 4 (6 animals per group) to study the regulatory T cells present among splenocytes.

As described in the paper by Faria et al., *Oral tolerance*, Immunol. Rev., 2005, 206(1), 232-259, regulatory T cells are a group of T cells that are key in the induction of oral tolerance, defined as a population involved in regulating the immune response, and they express CD4 and CD25 membrane markers.

The paper from 2003 by Hori et al., *Control of regulatory T cell development by the transcription factor Foxp*3, Science, 2003, 299(5609), 1057-61, describes that transcription factor Foxp3 is key for the development of regulatory T cells. For that reason it is considered that T cells with the CD4+CD25+Foxp3+ phenotype have a regulatory function.

The animals were sacrificed by means of cervical dislocation after inhalation anesthesia with isofluorane. The spleens were removed and splenocytes were obtained by means of mechanical disaggregation, filtration with cell strainers (BD Falcon Cell Strainer, Nylon, 40 μm), and erythrocyte lysis. CD4 and CD25 membrane splenocytes and intracellular Foxp3 were labeled by means of a regulatory T cell labeling kit (eBioscience) and analyzed by means of flow cytometry (BD LSR-Fortessa cell analyzer). The results were processed by means of the BD FACSdiva analysis software.

Figure 6:
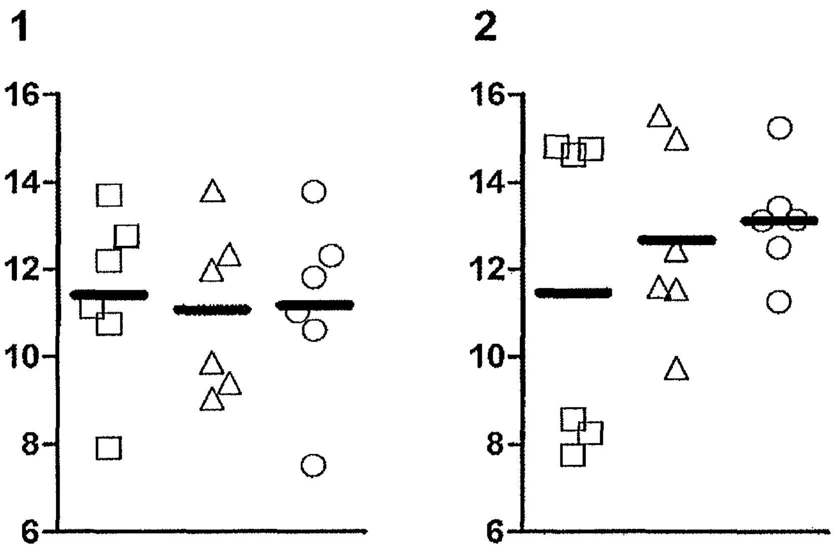
FIG. 6 depicts the percentages of regulatory T cells with the CD4+CD25+Foxp3+ phenotype with respect to total CD4+ T cells for each of the treatments with inactivated mycobacteria of *M. tuberculosis* and the control, at week 3 (graph 1) and at week 4 (graph 2) after infection. Said percentage of regulatory T cells is depicted on the y-axis. The different groups of animals are represented on the x-axis. The squares represent untreated animals (Control Group), the triangles represent animals in Group 1 treated before infection (prophylactic effect), and the circles represent animals in Group 2 treated after infection (therapeutic effect). The solid horizontal lines represent the arithmetic mean of each group. (Example 4)

FIG. 6 depicts the percentages of regulatory T cells, T cells with the CD4+CD25+Foxp3+ phenotype with respect to total CD4+ T cells, of the different treatments and the control, at week 3 (graph 1) and week 4 (graph 2) post-infection. The percentage of regulatory T cells is represented on the y-axis. The different types of treatment and the control are represented on the x-axis.

The squares represent untreated animals (Control Group), the triangles represent animals in Group 1, treated before infection, and the circles represent the animals in Group 2, treated after infection. Solid horizontal lines represent the arithmetic mean of each group.

It is observed that there is in fact an increase in the percentage of regulatory T cells between week 3 and week 4 only in the groups treated according to the tolerance-building regimen regardless of whether it was started before or after infection with *M. tuberculosis.*

Example 5

Oral Tolerance-Building Treatment with Inactivated Bacilli of *M. kansasii* Administered Before or after Infection (Prophylactic or Therapeutic Effect)

*Mycobacterium kansasii* is a slow-growing non-tuberculous *mycobacterium*. A clinical strain of *M. kansasii* (TOL) from the Unitat de Tuberculosi Experimental of Institut Germans Trias i Pujol strain collection, cultured in Proskauer Beck liquid medium until achieving exponential growth and a concentration of $8.07\times10^4$ colony forming units (CFUs) per ml was used to prepare the inactivated mycobacteria.

The culture was inactivated after autoclaving at 121° C. for 20 minutes and subsequently frozen at −80° C. It was subsequently diluted 50:50 in a 10% sucrose solution, packaged in vials in 2 ml volumes and preserved at −80° C.

Effectiveness of the inactivated mycobacteria was tested in 6-8 week old C3HeB/FeJ female mice free of specific pathogens.

A volume of 0.3 ml, corresponding to a 1:10 dilution, which corresponds to $2.42\times10^4$ CFUs, was administered in each dose.

The mice were split into three groups with 12 animals each, and each of the groups was subjected to the following tolerance-building protocol:

1) Control Group: Untreated.
2) Group 1 (pre-infection treatment): Treated orally by gavage, with 13 product doses containing the inactivated mycobacteria, administered 3 times a week (Monday, Wednesday and Friday). The group was infected 24 hours after administering the last dose.
3) Group 2 (post-infection treatment): 15 days after infection, the group was treated orally by gavage, with 13 product doses containing the inactivated mycobacteria, administered 3 times a week (Monday, Wednesday and Friday).

The virulent strain of *Mycobacterium tuberculosis* ($H_{37}Rv$ Pasteur), cultured in Proskauer-Beck medium to mid-logarithmic phase and preserved in 1 ml aliquots at a temperature of −70° C. until use, was used for infection.

The mice were endovenously infected by introducing an inoculum of about $2\times10^4$ viable bacilli.

The animals were observed and weighed daily until conditions of the animal required it be sacrificed, according to the same method described in Table 1 of Example 1.

Figure 7:
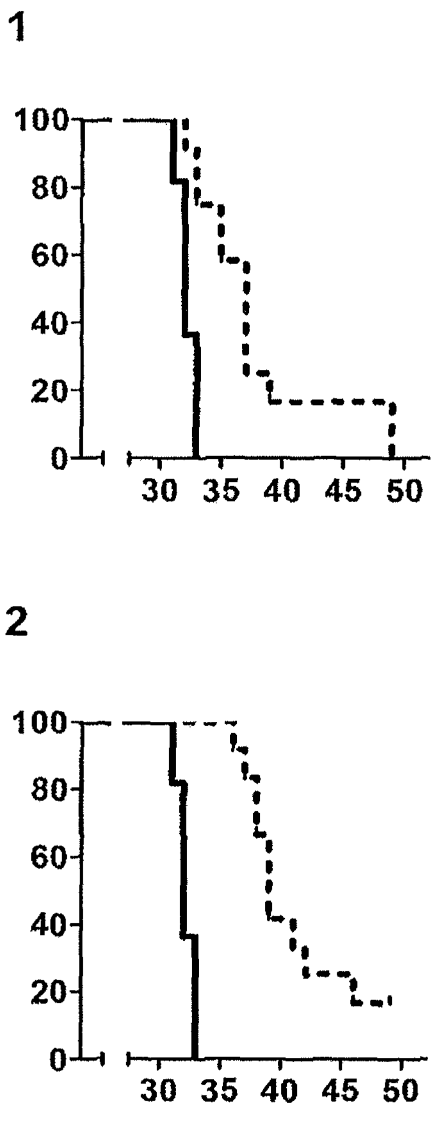
FIG. 7 shows the time of survival expressed in days represented on the x-axis and the percentage of surviving animals represented on the y-axis. In graph 1, the Control Group (solid line) is compared with Group 1 (discontinuous line) which was subjected to orally administered treatment with inactivated mycobacteria of *Mycobacterium kansasii* that started before infection (prophylactic effect). In graph 2, the Control Group (solid line) is compared with Group 2 (discontinuous line) which was subjected to orally administered treatment with inactivated mycobacteria of *Mycobacterium kansasii* that started after infection (therapeutic effect) (Example 5)

FIG. 7, graphs 1 and 2, show the results of survival of the different groups. Time of survival (in days) is represented on the x-axis, whereas the percentage of survivors is represented on the y-axis.

Graph 1 refers to prophylactic treatment, comparing the Control Group with Group 1, which was subjected to treatment that started before infection. It is observed that the Control Group (solid line) has a lower survival rate than Group 1 (discontinuous line), significant differences being observed (Log-rank test, $p<0.0001$; Gehan-Breslow-Wilcoxon test, $p<0.0001$).

Graph 2 refers to therapeutic treatment, comparing the Control Group with Group 2, which was subjected to treatment that started after infection. It is observed that the Control Group (solid line) has a lower survival rate than treated Group 2 (discontinuous line), significant differences being observed (Log-rank test, $p<0.0001$; Gehan-Breslow-Wilcoxon test, $p<0.0001$).

In both cases, the results reflect a protective response. It can therefore be concluded that oral treatment with tolerance-building regimens of slow-growing, non-tuberculous inactivated mycobacteria (*M. kansasii*), administered before or after infection by *M. tuberculosis*, increases the survival rate of the animals by delaying induction of the disease. It is therefore considered that the use of inactivated mycobacteria according to the invention is suitable as preventive treatment against tuberculosis by delaying conversion of the latent infection into the active infection.

Example 6

Oral Tolerance-Building Treatment with Inactivated Bacilli of *M. fortuitum*, Administered Before or after Infection (Prophylactic or Therapeutic Effect

*Mycobacterium fortuitum* is a fast-growing, non-tuberculous *mycobacterium*. An environmental strain of *M. fortuitum* (Manresa strain), from the Unitat de Tuberculosi Experimental of Institut Germans Trias i Pujol strain collection, cultured in Middlebrook 7H9 solid medium until achieving a concentration of $2\times10^9$ colony forming units (CFUs) per ml, was used to prepare the inactivated mycobacteria.

The culture was inactivated after autoclaving at 121° C. for 20 minutes and subsequently frozen at −80° C. It was subsequently diluted 50:50 in a 10% sterile sucrose solution, packaged in vials in 2 ml volumes and preserved at −80° C.

Effectiveness of the inactivated mycobacteria was tested in 6-8 week old C3HeB/FeJ female mice free of specific pathogens.

A volume of 0.3 ml corresponding to a 1:1000 dilution, which corresponds to $6\times10^5$ CFUs, was administered in each dose.

The mice were split into three groups with 12 animals each, and each of the groups was subjected to the following tolerance-building protocol:

1) Control Group: Untreated.
2) Group 1 (pre-infection treatment): Treated orally by gavage, with 10 product doses containing the inactivated mycobacteria, administered 5 times a week (Monday to Friday). The group was infected 24 hours after administering the last dose.
3) Group 2 (post-infection treatment): Treated orally by gavage, with 10 product doses containing the inactivated mycobacteria, administered 5 times a week (Monday to Friday), starting the treatment 5 days after infection.

The virulent strain of *Mycobacterium tuberculosis* ($H_{37}Rv$ Pasteur), cultured in Proskauer-Beck medium to mid-logarithmic phase and preserved in 1 ml aliquots at a temperature of −70° C. until use, was used for infection.

The mice were endovenously infected by introducing an inoculum of about $2\times10^5$ viable bacilli.

The animals were observed and weighed daily until conditions of the animal required it be sacrificed, according to the same method described in Table 1 of Example 1.

Figure 8:
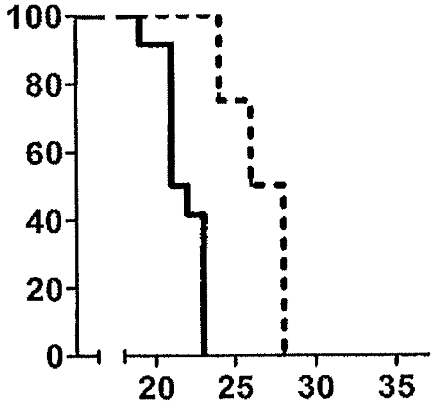
FIG. 8 shows the time of survival expressed in days represented on the x-axis and the percentage of surviving animals represented on the y-axis. In graph 1, the Control Group (solid line) is compared with Group 1 (discontinuous line) which was subjected to orally administered treatment with inactivated mycobacteria of *Mycobacterium fortuitum* that started before infection (prophylactic effect). In graph 2, the Control Group (solid line) is compared with Group 2 (discontinuous line) which was subjected to orally administered treatment with inactivated mycobacteria of *Mycobacterium fortuitum* that started after infection (therapeutic effect). (Example 6)
Figure 8:
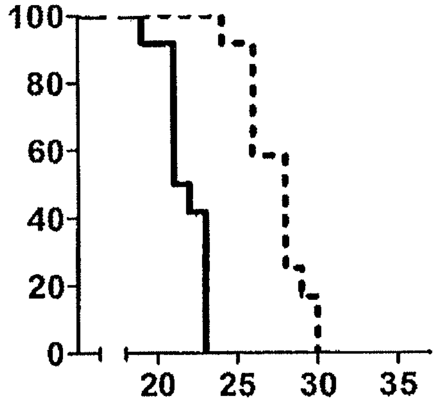

FIG. 8, graphs 1 and 2, show the results of survival of the different groups. Time of survival (in days) is represented on the x-axis, whereas the percentage of survivors is represented on the y-axis.

The results obtained as regards prophylactic treatment are shown in graph 1. It is observed that the Control Group (solid line) has a lower survival rate than treated Group 1 (discontinuous line), significant differences being observed (Log-rank test, $p<0.0001$; Gehan-Breslow-Wilcoxon test, $p<0.0001$).

The results obtained as regards therapeutic treatment are shown in graph 2. It is observed that the Control Group (solid line) has a lower survival rate than treated Group 2 (discontinuous line), significant differences being observed (Log-rank test, $p<0.0001$; Gehan-Breslow-Wilcoxon test, $p<0.0001$).

In both cases, the results reflect a protective response. It can therefore be concluded that oral administration of tolerance-building regimens of fast-growing, non-tuberculous mycobacteria (*M. fortuitum*), before or after infection by *M. tuberculosis*, increases the survival rate of the animals by delaying induction of the disease. It is therefore considered that the use of inactivated mycobacteria according to the invention is suitable as preventive treatment against tuberculosis by delaying conversion of the latent infection into the active infection.

Example 7

Oral Tolerance-Building Treatment with Inactivated Bacilli of *M. fortuitum*, Administered after Treatment of Experimental Active Tuberculosis (Effect Against the Relapse)

Inactivated bacilli of *M. fortuitum* (Manresa strain) were prepared following the same method described in Example 6.

Effectiveness of the inactivated mycobacteria was tested in 6-8 week old C3HeB/FeJ female mice free of specific pathogens.

A volume of 0.3 ml corresponding to a 1:100 dilution, which corresponds to $6\times10^6$ CFUs, was administered in each dose.

In this case, effectiveness of the preventive tolerance-building treatment according to the invention was studied as regards the anti-relapse effect, i.e., after the animals developed active tuberculosis and after they were treated with anti-tuberculous drugs.

Therefore, at the beginning of the experiment, the mice were endovenously infected by introducing an inoculum of about $2\times10^5$ viable bacilli.

Like in the preceding examples, the virulent strain of *Mycobacterium tuberculosis* ($H_{37}Rv$ Pasteur), cultured in Proskauer-Beck medium to mid-logarithmic phase and preserved in 1 ml aliquots at a temperature of −70° C. until use, was used for infection.

The animals were observed and weighed daily until the conditions of the animal indicated that the animal be sacrificed, according to the same method described in Table 1 of Example 1.

At this time (day 21), treatment was started using the antibiotic combination contained in the commercial preparation called RIMSTAR (isoniazid, ethambutol, pyrazinamide and rifampicin), adjusted to the animal's weight, 5 days a week. The last dose was administered on day 60.

The mice were then split into two groups with 12 animals each, and each of the groups was subjected to the following tolerance-building protocol:

1) Control Group: Without tolerance-building treatment.
2) Group 1: Treated orally by gavage, with 14 product doses containing the inactivated mycobacteria, administered 7 times a week (Monday to Sunday), starting said tolerance-building treatment 72 hours after ending treatment for active tuberculosis with RIMSTAR (day 63), and administering the last dose on day 76.

Figure 9:
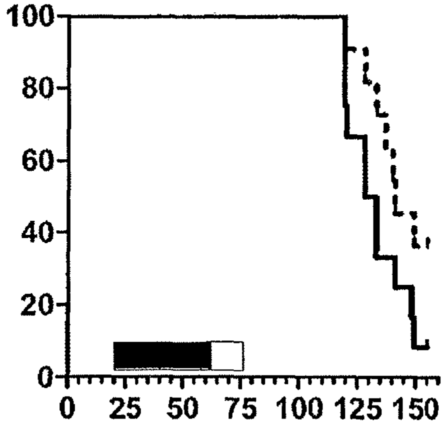
FIG. 9 shows the time of survival expressed in days represented on the x-axis and the percentage of surviving animals represented on the y-axis. The animals were infected and then treated with the anti-tuberculous drug RIMSTAR. After treatment with RIMSTAR, Group 1 was subjected to subsequent orally administered tolerance-building treatment with inactivated mycobacteria of *Mycobacterium fortuitum* (anti-relapse effect). The Control Group (solid line, without tolerance-building treatment) is compared with Group 1 (discontinuous line, with tolerance-building treatment). Treatment periods with RIMSTAR treatment (black rectangle) and with subsequent tolerance-building treatment (white rectangle) are indicated on the x-axis. (Example 7).

The results obtained as regards treatment against relapse are graphically depicted in FIG. 9. Time of survival (in days) is represented on the x-axis, whereas the percentage of survivors is represented on the y-axis. Furthermore, on the temporal x-axis, the treatment period with RIMSTAR is indicated with a black rectangle and the period with the tolerance-building treatment of Group 1 is indicated with a white rectangle.

It is observed that the Control Group (solid line) has a lower survival rate than treated Group 1 (discontinuous line).

The results reflect a protective response, and it can therefore be concluded that oral administration of tolerance-building regimens of mycobacteria prevents relapse after receiving treatment for active tuberculosis.

The invention claimed is:

1. A method for preventing tuberculosis in an individual comprising administering to the individual a medicinal product comprised of inactivated mycobacteria that are inactivated by means of a heating process, wherein:

doses of the medicinal product comprised of inactivated mycobacteria are periodically administered orally, the interval between doses is not more than 5 days, and the number of doses administered is at least 5.

2. The method according to claim 1, wherein the inactivated mycobacteria are selected from the group consisting of *M. tuberculosis, M. bovis, M. africanum*, and *M. microti, M. bovis* BCG, *M. fortuitum* and *M. kansasii.*

3. The method according to claim 2, wherein the inactivated mycobacteria are selected from *M. tuberculosis, M. bovis, M. bovis* BCG, *M. fortuitum* and *M. kansasii.*

4. The method according to claim 1, wherein the interval between doses is not more than 3 days.

5. The method according to claim 4, wherein the interval between doses is not more than 2 days.

6. The method according to claim 1, wherein the number of doses administered is at least 7.

7. The method according to claim 6, wherein the number of doses administered is at least 9.

8. The method according to claim 1, wherein the each dose comprises between $10^3$ and $10^{10}$ inactivated mycobacteria.

9. The method according to claim 1, wherein the inactivated mycobacteria are administered in the form of a pharmaceutical composition comprising the inactivated mycobacteria and at least one pharmaceutically acceptable excipient.

10. The method according to claim 9, wherein the pharmaceutical composition is in capsule form.

11. The method according to claim 9, wherein the pharmaceutical composition is in tablet form.

12. The method according to claim 1, wherein the medicinal product is administered to an individual infected by *M. tuberculosis* in which the infection is in a latent state.

13. The method according to claim 12, wherein the individual had previously developed active tuberculosis.

14. The method according to claim 1, wherein the medicinal product is administered to an individual not infected by *M. tuberculosis.*

* * * * *